(12) United States Patent
Chiarello et al.

(10) Patent No.: US 9,024,252 B2
(45) Date of Patent: May 5, 2015

(54) OPTICAL SENSOR APPARATUS TO DETECT LIGHT BASED ON THE REFRACTIVE INDEX OF A SAMPLE

(75) Inventors: Ronald Chiarello, Lafayette, CA (US); Shad Pierson, Walnut Creek, CA (US); Christopher Wacinski, Walnut Creek, CA (US); Mark Arbore, Los Altos, CA (US); Yevgeny Anoikin, Fremont, CA (US)

(73) Assignee: Entegris-Jetalon Solutions, Inc., Billerica, MA (US)

( * ) Notice: Subject to any disclaimer, the term of this patent is extended or adjusted under 35 U.S.C. 154(b) by 307 days.

(21) Appl. No.: 13/401,765

(22) Filed: Feb. 21, 2012

(65) Prior Publication Data

US 2013/0214138 A1 Aug. 22, 2013

(51) Int. Cl.
*H01J 5/02* (2006.01)
*G01N 21/43* (2006.01)

(52) U.S. Cl.
CPC ........ *G01N 21/431* (2013.01); *G01N 2021/434* (2013.01); *G01N 2021/437* (2013.01)

(58) Field of Classification Search
USPC ........ 250/216, 239, 551, 208.1, 559.4; 385/9, 385/11, 13; 356/128–137, 244–246, 356/436–448
See application file for complete search history.

(56) References Cited

U.S. PATENT DOCUMENTS

| | | |
|---|---|---|
| 4,699,511 A | 10/1987 | Seaver |
| 5,101,099 A * | 3/1992 | Funada et al. ............. 250/208.1 |
| 5,373,366 A | 12/1994 | Bowers |
| 5,563,707 A | 10/1996 | Prass et al. |
| 5,694,210 A | 12/1997 | Newell et al. |
| 6,097,479 A | 8/2000 | Melendez et al. |
| 6,277,330 B1 | 8/2001 | Liu et al. |
| 6,549,276 B1 | 4/2003 | Longtin |
| 6,594,018 B1 | 7/2003 | Bartholomew |

(Continued)

FOREIGN PATENT DOCUMENTS

| | | |
|---|---|---|
| TW | 408220 | 10/2000 |
| TW | 1226436 | 1/2005 |
| WO | WO2010/055280 | 5/2010 |

OTHER PUBLICATIONS

International Search Report and Written Opinion issued for PCT Application No. PCT/US2013/026329, mailed Apr. 23, 2013, 7 pages.

(Continued)

*Primary Examiner* — Que T Le
(74) *Attorney, Agent, or Firm* — Sprinkle IP Law Group

(57) ABSTRACT

An optical sensor apparatus includes an optically transmissive structure having planar first, second, and third faces, two or more light sources located outside the structure adjacent the first face, and a photodetector array located outside the prism adjacent the first face. The structure, light sources, and photodetector array are configured such that light from the light sources that is totally internally reflected at an optical interface between the prism and a sample outside the structure proximate the second face is reflected at the third face and incident on a portion of the photodetector array that depends on a refractive index of the sample. The light sources are positioned with respect to the structure and photodetector array such that the totally internally reflected light from each light source corresponds to a different range of refractive index of the sample and maps to a corresponding portion of the photodetector array.

15 Claims, 3 Drawing Sheets

(56) References Cited

U.S. PATENT DOCUMENTS

| | | |
|---|---|---|
| 6,762,832 B2 | 7/2004 | Fisher et al. |
| 6,803,594 B2 | 10/2004 | Spolaczyk et al. |
| 6,931,219 B2 | 8/2005 | Viturro et al. |
| 6,943,878 B2 | 9/2005 | Fisher et al. |
| 7,194,216 B2 | 3/2007 | Borton et al. |
| 7,221,440 B2 | 5/2007 | McCann et al. |
| 7,268,864 B2 | 9/2007 | Chiarello et al. |
| 7,271,883 B2 | 9/2007 | Newell et al. |
| 7,359,055 B2 | 4/2008 | Schneider |
| 7,492,447 B2 | 2/2009 | Nakajima et al. |
| 7,498,145 B2 | 3/2009 | Uchiyama et al. |
| 7,602,492 B2 | 10/2009 | Do |
| 7,602,496 B2 | 10/2009 | Harsh et al. |
| 7,652,767 B2 | 1/2010 | Harsh et al. |
| 7,688,450 B2 | 3/2010 | Lei |
| 8,045,172 B2 | 10/2011 | Egger |
| 2010/0220318 A1 | 9/2010 | Moll et al. |

OTHER PUBLICATIONS

Office Action issued for Taiwanese Patent Application No. 102105587, mailed Jul. 25, 2014, 9 pages.

\* cited by examiner

OPTICAL SENSOR APPARATUS TO DETECT LIGHT BASED ON THE REFRACTIVE INDEX OF A SAMPLE

FIELD OF THE INVENTION

Embodiments of the present invention are related to optical sensors and more specifically to optical sensors that measure index of refraction of a sample by sensing total internal reflection at an interface between an optical material and the sample.

BACKGROUND OF THE INVENTION

Systems for refractive index measurement of a sample using the critical angle are well known in the art, as are the principles of physics underlying the measurement of critical angle to determine refractive index of a medium. When light traveling from a high index medium is incident upon an interface between the high index medium and another medium having a lower refractive index at angles of incidence larger than a critical angle of incidence, total internal reflection may be observed. The critical angle is a function of the refractive index of both media. However, if the refractive index of one medium is known, the refractive index of the other may be determined from a measurement of the critical angle $\theta_c$ using the well-known formula:

$$\sin\theta_c = \frac{n_2}{n_1}.$$

Where $n_1$ is the refractive index of the high index medium and $n_2$ is the refractive index for the low index medium. By convention, the critical angle of incidence is measured with respect to a line perpendicular to the interface between the two media.

U.S. Pat. No. 6,097,479 describes a sensor for making critical angle measurements in which a light source and photodetector array are encapsulated in a light transmissive housing that acts as the high index medium. The housing forms a prism having one face in contact with a sample, which acts as the low index medium. Light from the light source is incident on an interface between the sample and the prism over a range of incident angles. A portion of the light that is incident on the interface at angles greater than a critical angle undergoes total internal reflection and is detected by the photodetector array. Different parts of the photodetector array are therefore illuminated by the totally internally reflected light depending on the critical angle, which depends on the index of refraction of the prism and of the sample. The pattern of illumination of the photodetector array can be analyzed to determine the index of refraction of the sample.

It is within this context that embodiments of the present invention arise.

BRIEF DESCRIPTION OF THE DRAWINGS

The teachings of the present invention can be readily understood by considering the following detailed description in conjunction with the accompanying drawings, in which.

DESCRIPTION OF THE SPECIFIC EMBODIMENTS

Figure 1A:
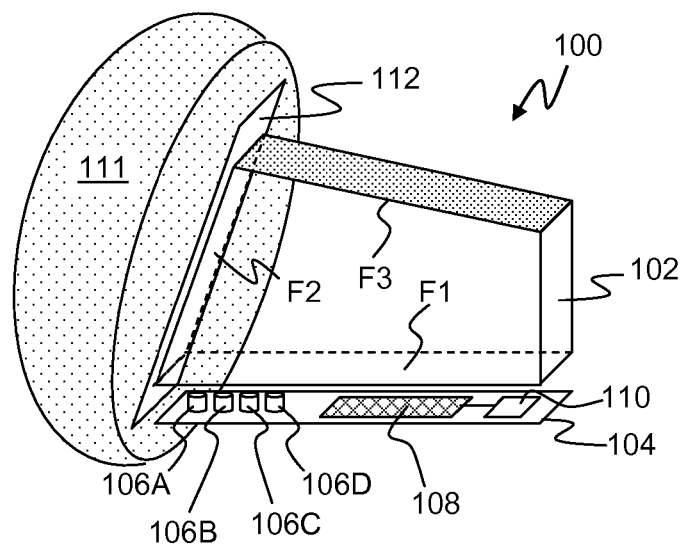
FIG. 1A is a three-dimensional schematic diagram of an optical sensor apparatus according to an embodiment of the present invention.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., may sometimes be used with reference to the orientation of the figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

GLOSSARY

As used herein, the following terms have the following meanings.

Coefficient of Thermal Expansion refers to a property of a material that quantifies a change in one or more physical dimensions of the material with change in temperature.

CTE-matched refers to materials having similar coefficients of thermal expansion (CTE). For the purposes of the present application two materials can be said to be CTE-matched if their coefficients of thermal expansion are within about a factor of 2 of each other.

Dispersion (or optical dispersion) refers to a phenomenon by which a wave separates into spectral components with different frequencies, due to a dependence of the wave's speed on its frequency when the wave travels in a material. In optics this may be expressed as a dependence of the refractive index of the material on the vacuum wavelength of light.

Index of Refraction (or refractive index) refers to an optical property of a material that is generally defined as the ratio of the speed of light in vacuum (or other reference medium) to the speed of light in the material.

Infrared Radiation refers to electromagnetic radiation characterized by a vacuum wavelength between about 700 nanometers (nm) and about 100,000 nm.

Light generally refers to electromagnetic radiation in a range of frequencies running from infrared through the ultraviolet, roughly corresponding to a range of vacuum wavelengths from about 1 nanometer ($10^{-9}$ meters) to about 100 microns.

Sapphire generally refers an anisotropic, rhombohedral crystal form of Aluminum Oxide ($Al_2O_3$).

Total Internal Reflection refers to a phenomenon in which electromagnetic radiation in a given medium which is incident on an interface with medium having a lower index of refraction at an angle greater than a critical angle is completely reflected from the boundary. By convention, the critical angle of incidence is measured with respect to a line perpendicular to the interface between the two media. If the angle of incidence is measured with respect to a line tangent to the interface, then total internal reflection occurs for angles of incidence less than the critical angle.

Ultraviolet (UV) Radiation refers to electromagnetic radiation characterized by a vacuum wavelength shorter than that of the visible region, but longer than that of soft X-rays. Ultraviolet radiation may be subdivided into the following wavelength ranges: near UV, from about 380 nm to about 200 nm; far or vacuum UV (FUV or VUV), from about 200 nm to about 10 nm; and extreme UV (EUV or XUV), from about 1 nm to about 31 nm.

Vacuum Wavelength refers to the wavelength electromagnetic radiation of a given frequency would have if the radiation were propagating through a vacuum and is given by the speed of light in vacuum divided by the frequency.

Visible Light refers to electromagnetic radiation characterized by a vacuum wavelength shorter than that of the IR radiation, but longer than that of UV radiation, the visible range is generally regarded to be from about 400 nm to about 700 nm.

INTRODUCTION

Many prior art refractive index sensors that are based on measurements of critical angle encapsulate the light source and the photodetector array in the material, e.g., transparent epoxy, that forms the prism. One drawback to prior refractive index sensors is that they typically use only one light source that provides one wavelength of light used for refractive index measurements. This has several disadvantages. First, the single light source can limit the range of angles of incidence and therefore the range of refractive index that can be measured. Secondly, a single light source can limit the resolution of sensor.

Another drawback to prior art refractive index sensors is that the light source and photodetector array are combined with the prism in an integrated design in which an optical epoxy encapsulates both the light source and the photodetector array. Designs that use epoxy encapsulation suffer from degradation of epoxy starting at temperatures of about 85 C.°, limiting the range of processes that can be measured. Certain existing sensor designs use refractive index-matching plastic prisms that are chemically incompatible with many fluids or chemicals. Such designs require an intervening, chemically compatible material at the measurement interface. In addition, plastic prisms preclude the use of short wavelength light.

Another disadvantage arises from the fact that often the interface with the sample is not a face of the prism but is instead a "window" made of glass or other optically dense material that is glued to one of the faces of the prism. However, there is a significant mismatch in coefficient of thermal expansion (CTE) between optical epoxies used for the prism in prior refractive index sensors and the typical material (e.g., borosilicate glass) that is used for the window. For example, a typical optical epoxy has a CTE of about 50 parts per million per centigrade degree (50 ppm/C.°). Borosilicate glass has a CTE of about 7 ppm/C.°, which is about seven times smaller. A common optical grade of borosilicate glass is sold commercially under the name Schott BK-7.

The CTE mismatch between the window and the optical epoxy can lead to problems when the fluid being sampled is at a temperature that is significantly hotter or colder than room temperature.

According to embodiments of the present invention an optical sensor apparatus may include features that overcome the disadvantages of prior art refractive index sensors.

Optical Sensor Apparatus

According an embodiment of the present invention an optical sensor apparatus of a new design uses an optical waveguide structure made of a precision-machined, unitary, optically transparent material, which simultaneously forms a measurement interface and interfaces with light sources and a photodetector array.

The use of a light guiding structure made from a precision-machined optically transparent material allows the use of a wider range of wavelengths than is possible with a plastic prism. The solid precision-machined optically transparent material allows for the direct deposition of a reflecting material onto the light guiding structure, eliminating the need to mechanically place a mirror on a prism. This reduces design complexity and improves optical signal.

The two common-wavelength light sources (e.g., yellow LEDs) significantly extend the RI range that can be measured compared to previous RI sensor designs. Light from the two common-wavelength light sources overlaps in a center of the RI range, which increases signal to noise ratio.

Figure 1B:
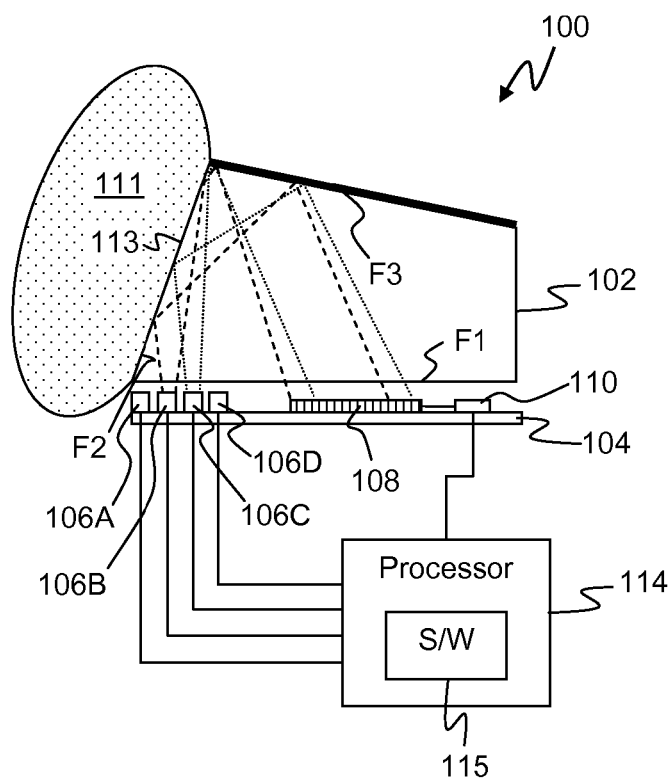
FIG. 1B is a side-view schematic diagram of an optical sensor apparatus according to an embodiment of the present invention.

FIG. 1A and FIG. 1B illustrate examples an optical sensor apparatus 100 according to an embodiment of the present invention. The optical sensor apparatus 100 is based on a reflection geometry. The apparatus 100 generally includes a light guiding structure 102 made of an optically dense material such as borosilicate glass, or sapphire. Alternatively, the light guiding structure 102 may be made of quartz, diamond, undoped yttrium aluminum garnet (YAG), calcium carbonate, or any other optically transparent material. The light guiding structure has at least three faces F1, F2 and F3. The light guiding structure 102 may be attached to a printed circuit board 104 by any suitable means, e.g., mechanical attachment, epoxy, fusing, etc. Two or more light sources 106A, 106B, 106C, 106D and a photodetector array 108 are attached to the printed circuit board 104. By way of example and not by way of limitation, each light source may be a light emitting diode (LED). Other non-limiting examples of light sources include solid state lasers and semiconductor lasers. By way of example, and not by way of limitation, the light guiding structure 102 may be in the form of a prism made of an optically transmissive medium or material, as shown in FIG. 1A and FIG. 1B. However, embodiments of the invention are not limited to those that utilize a prism to provide the desired light guiding function. Other geometries and components may be used to provide the desired reflection geometry for the sensor apparatus 100.

Figure 2:
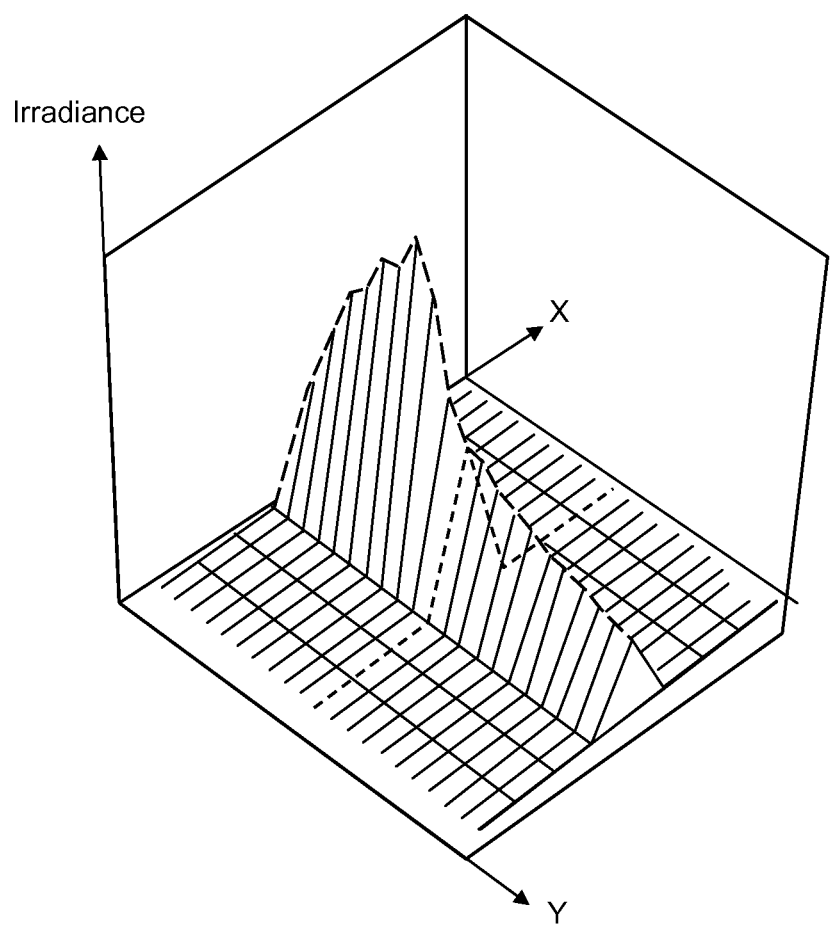
FIG. 2 is a three-dimensional graph illustrating a photodetector array signal in an optical apparatus according to an embodiment of the present invention.

The photodetector array 108 is generally a position sensitive detector that any array of light sensing elements can produce signals that vary depending on how much light is received at different parts of the array. The signals may be analog or digital electrical signals. By way of example and not by way of limitation, the photodetector array may be a photodiode array. Alternatively, an array of charge coupled devices, photoresistors, and arrays of other types of light sensing elements may be used in the photodetector array. In general, each light sensing element in the array may provide a signal that corresponds to the irradiance (optical power per unit area) at that element. Each light sensing element thus provides a irradiance signal for a corresponding "pixel", e.g., as shown in FIG. 2. An optional memory 110, e.g., in the form of an integrated circuit, may be coupled to the photodetector array 108 to temporarily store the pixel signals produced by the photodetector array. By way of example, and not by way of limitation, the memory 110 may be a flash memory or electrically erasable programmable read-only memory (EEPROM).

As seen in FIG. 1B, light from the light sources is emitted over a range of angles. The light emitted from the light sources passes through the first face F1. At least some of the light that passes through the first face F1 undergoes total internal reflection at an interface with a sample 111 proximate the second face F2. The first face F1 may be coated with an anti-reflection (AR) coating. The light that is totally internally reflected at the interface is sometimes referred to herein as "totally internally reflected light". In the example depicted in FIG. 1A, a window 112 is attached to the second face F2 and the interface is the side of the window that is in contact with the sample. It is noted that the window 112 is optional. If the window is omitted, as in the example depicted in FIG. 1B, the interface 113 with the sample 111 may be located at the second face F2.

The totally internally reflected light from the interface with the sample is reflected at a third face F3 and passes back through the first face F1 to the photodetector array 108. The prism 102 thus maps some of the cone of light from each of the light sources 106A, 106B, 106C, 106D onto the photodetector array 108. The index of refraction of the sample and the offset between the light sources determines which portion of each cone of light will be totally internally reflected at the interface with the sample.

In some embodiments, the material of the prism 102 may be selected such that total internal reflection takes place at the third face F3. Alternatively, the third face F3 may be coated with a metal or dielectric reflective coating to facilitate reflection of the light incident on the third face F3 from inside the prism 102.

To facilitate computation of the index of refraction, the apparatus 100 may further include a processor 114 coupled to the photodetector array 108 and/or the memory 110. The processor 114 may also be coupled to the light sources 106A, 106B, 106C, 106D and may be configured to selectively control which light source is turned on and which light source is turned off. The processor 114 may be configured, e.g., by programming with suitable executable instructions 115, to analyze the irradiance pattern measured by the photodetector array and determine the critical angle at the interface with the sample and the corresponding index of refraction. Specifically, the processor may analyze the irradiance pattern to determine the pixel location of a telltale feature in the pattern indicative of light reflected at the interface with the sample 111 at the critical angle. The pixel location of the telltale feature may then be correlated to the index of refraction either by analysis from first principles from the known geometry and material properties of the components of the apparatus 100 or from a simple calibration using measurements of one or more materials of known refractive index.

The critical angle may be determined from the irradiance pattern as follows. For angles of incidence below the critical angle, some light will be refracted at the interface with the sample 111 into the sample and some will be reflected to the photodetector array 108. At the critical angle, the refracted light is refracted along the interface. For angles greater than the critical angle all of the light is reflected at the interface with the sample 111. The light rays corresponding to light reflected at the critical angle can be identified by a transition between low intensity and high intensity in the pattern of irradiance at the photodetector array. The pixel location of the transition can be correlated to critical angle from the known geometry and refractive indices of the light guiding structure 102 and window 112 and from the known locations of the light source(s) and the photodetector array 108. Alternatively, the pixel location of the transition may be calibrated against refractive index using several samples of known refractive index. The light sources 106A, 106B, 106C, 106D may include two or more light sources that emit light at a common wavelength (referred to herein as "common-wavelength light sources") and/or two or more light sources that emit light at different wavelengths. By way of example, and not by way of limitation, the optical sensor apparatus 100 may include four light emitting diodes. Two LEDs may be configured to emit light of a common wavelength and two other LEDs may be configured to emit light of different wavelengths.

Using two light sources that emit light at the same wavelength allows changing scale so that the photodetector array 108 can be overfilled, i.e., filled with totally internally reflected light beyond the extent possible with a single light source. The common-wavelength light sources may be configured such that cones of totally internally reflected light from the different common-wavelength light sources overlap at the photodetector array to some extent. The use of two common-wavelength light sources provides for a larger refractive index range. The extra common-wavelength light source gives a greater number of resolvable refractive indices that can be detected, which can provide greater refractive index range or better resolution or a combination of both depending on how the common-wavelength light sources are configured to fill the photodetector array.

For example as shown in FIG. 1B, suppose that light sources 106B and 106C are the common-wavelength light sources. The cone of light from light source 106B that undergoes total internal reflection at the interface is indicated by dashed lines. The cone of light from light source 106C that undergoes total internal reflection at the interface is indicated by dotted lines. In this example, the cones of totally internally reflected light from the two light sources 106B, 106C are mapped to two corresponding regions of the photodetector array labeled RB and RC. Because of the different locations of the light sources 106A, 106B, light from these two sources is totally internally reflected at the interface with the sample 111 over different ranges of incident angles. These different ranges of incident angles translate into different patterns of irradiance at the photodetector array. If the positions of the light sources 106B, 106C, the geometry and refractive index of the prism 102, are known, it is possible to determine the index of refraction for the sample 111 by analyzing the irradiance pattern at the photodetector array 108, as discussed above.

In the apparatus 100 depicted in FIG. 1B, light sources 106A and 106D may emit light at vacuum wavelengths different from each other and also different from the vacuum wavelength of the light emitted by common-wavelength light sources 106B, 106C. In one particular non-limiting implementation the two common wavelength LEDs may both emit yellow light, corresponding to a vacuum wavelength of about 589 nm. One non-common wavelength LEDs may emit ultraviolet light, e.g., at a vacuum wavelength of about 375 nm and the other non-common wavelength LED may emit infrared light, e.g., at a vacuum wavelength of about 940 nm.

By including two or more light sources that emit light at two or more different wavelengths the apparatus 100 can be used to estimate optical dispersion of the sample. Since the dispersion of a material is a property characteristic of the type of material, measuring dispersion can be used to distinguish between one material and another. By way of example, the processor 114 may be configured, e.g., by suitable programming, to determine an optical dispersion of the sample 111 by analyzing irradiance measurements obtained by the photodetector array 108 when light from the light sources 106A, 106D that is totally internally reflected at the interface with the sample 111. The light sources 106A, 106D may be turned on at the same time or may alternatively be turned on one at a time for sequential measurements. It is noted that by using multiple light sources emitting at different wavelengths the apparatus 100 may avoid the need for optical filters to obtain different wavelengths from a single light source. Eliminating the need for optical filters reduces design and mechanical complexity, and improves power efficiency. A more compact design is also possible by eliminating optical filters. In addition signal to noise ratio (SNR) can be improved by using multiple light sources. A larger range of wavelengths is possible with multiple light sources because the (wavelength) range of a single light source may be limited.

There are a number of different ways in which optical dispersion measurements made with the sensor apparatus 100 may be used. By way of example, and not by way of limitation, if the sensor apparatus 100 is used to measure the refractive index of a solution having a known solvent (e.g., water ($H_2O$)) and known solute (e.g., hydrogen peroxide ($H_2O_2$)) measurements of refractive index n versus vacuum wavelength may be used to estimate the concentration of solute.

In certain embodiments of the present invention there may be a free-space gap g between light sources 106A, 106B, 106C, 106D and the prism 102 or between prism 102 and the photodetector array 108 or both. The free-space gap allows some flexibility in the design of the sensor apparatus since the photodetector array and light source are not both encapsulated by the prism material. The free space gap also allows an additional degree of flexibility in optimizing the irradiance fill pattern at the photodetector array for multiple light sources. In addition, a free-space gap (e.g., an air gap) is less susceptible to degradation than epoxy.

The light guiding structure 102 may be made of a rigid optical material, such as sapphire, BK7, or an undoped garnet such as undoped Yttrium-Aluminum Garnet (YAG). If used without a window 112, the refractive index of the light guiding structure 102 must generally be larger than the highest refractive index that the apparatus 100 is expected to measure. Alternatively, if a window is used, it may be desirable for the refractive index of the window 112 to be greater than the refractive index of the light guiding structure 102 in order to avoid total internal reflection at the interface between the prism and the window. However, this is not always the case. For example, a free electron metal may be placed at the interface 111 making the sensor apparatus 100 a surface plasmon resonance sensor, which as a practical matter, may act as a refractive index sensor. Furthermore, the adhesive used to attached the window 112 to the light guiding structure 102 may be one that has a higher refractive index than the material of the structure 102 but a lower refractive index than the material of the window 112. In some embodiments, it may also be desirable for the adhesive to have a refractive index that is higher than the largest refractive index that the apparatus 100 is expected to measure.

The window 112 is optional, but for many applications it is preferred. The light guiding structure 102 can be glued directly to the window 112 or vice versa, e.g., using a suitable optical adhesive. Alternatively, the window may be attached to the light guiding structure (or vice versa) using a mechanical seal with a refractive index matched gel or oil. The light guiding structure may alternatively be fused to the window. The material of the light guiding structure 102 may be chosen to be CTE-matched to the material of the window 112. By way of example, and not by way of limitation, the prism may be made of borosilicate glass having a CTE of 7.1 ppm/C.° and sapphire having a CTE in the c-plane (the plane perpendicular to the c-axis) of 4.5 ppm/C.°. In such a case, the CTE of the prism would be about 1.6 times larger than the CTE of the window, which is sufficiently small that the prism and window can be said to be CTE matched.

It is further noted for the adhesive used to attach the window to the prism to be sufficiently complaint to accommodate the CTE of difference between the prism and window materials. By way of example, and not by way of limitation, for a prism made of borosilicate glass and a sapphire window, a suitable UV-curing polymer adhesive is sold commercially under the name Norland Optical Adhesive 61 (or NOA 61), and is available from Norland Products of Cranbury, N.J. It is further noted that NOA 61 has a refractive index between that of borosilicate glass and sapphire.

It is also desirable for the prism material to be CTE-matched to the material of the printed circuit board 104. By way of example, the printed circuit board may be made of a glass reinforced epoxy composite material such as FR4, which as a CTE of about 11 ppm/C.°, which is sufficiently close to the CTE of borosilicate glass to be considered CTE-matched for the purposes of embodiments of the present invention.

Figure 3A:
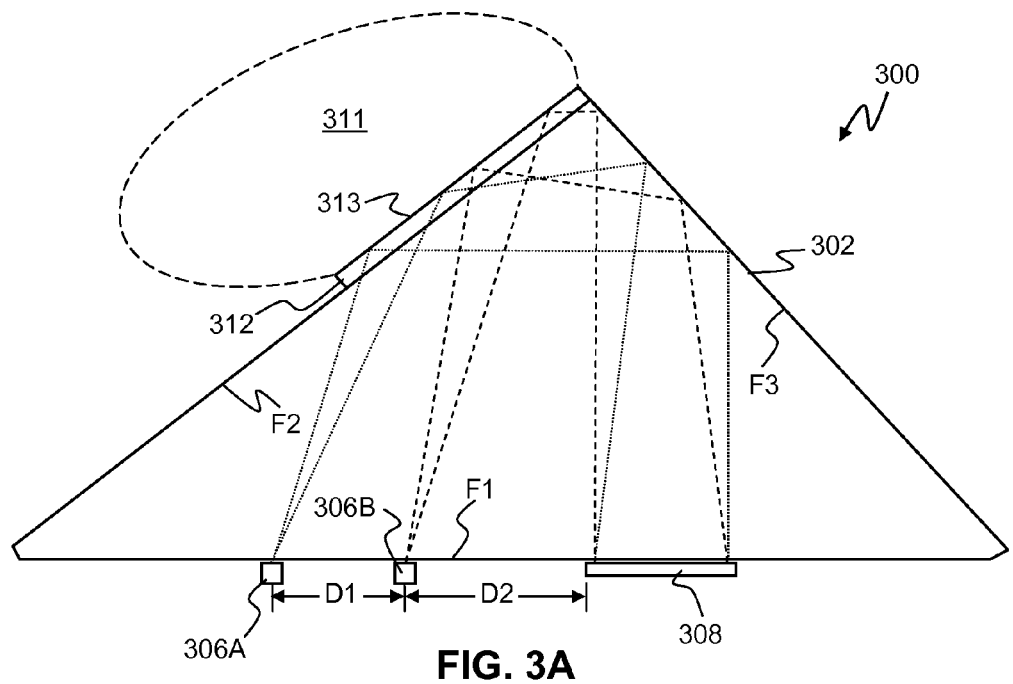
FIG. 3A is a side view schematic diagram illustrating an optical sensor apparatus according to an alternative embodiment of the present invention.
Figure 3B:
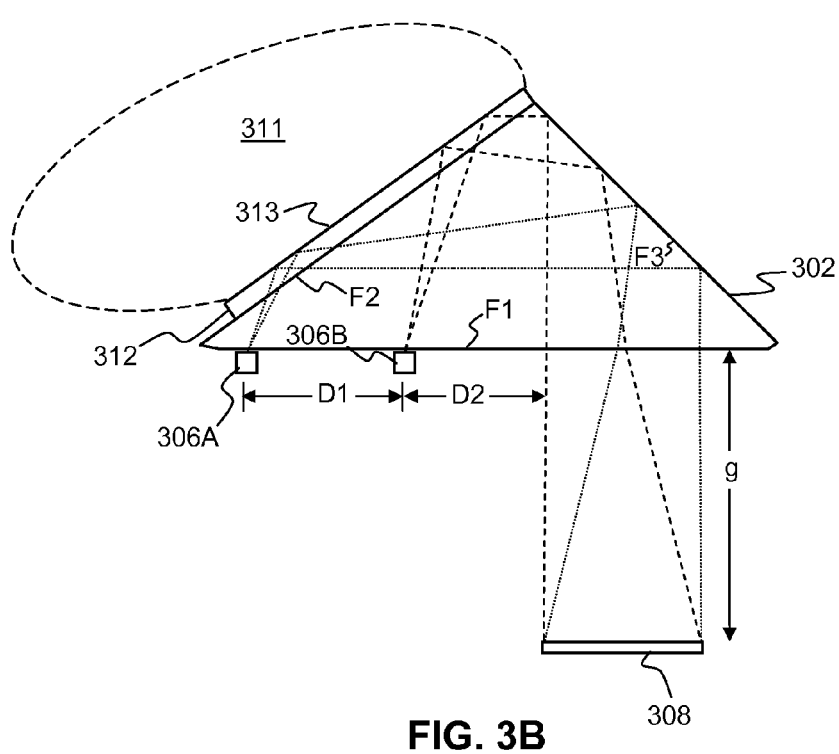
FIG. 3B is a side view schematic diagram illustrating an optical sensor apparatus according to another alternative embodiment of the present invention.

A number of variations are possible on the embodiments described above. Two possible variations, among others, are shown in FIG. 3A and FIG. 3B. As shown in FIG. 3A, in an optical sensor apparatus 300 light sources 306A, 306B and a photodetector array 308 may be located in an approximately co-planar configuration proximate a first face F1 of a large light guiding structure 302. The first face F1 may be coated with an anti-reflection (AR) coating. Light from the sources 306A, 306B passes through the first face F1 toward a window 312 attached to a second face F2. Total internal reflection occurs at an interface 313 between the window 312 and a sample 311 over corresponding ranges of angles of incidence for each light source 306A, 306B. A portion of the totally internally reflected light is reflected at a third face F3 and passes back through the first face F1 to the photodetector 308. If the prism 312 is made of a material with a relatively high refractive index, e.g., about 1.7 or greater, light totally internally reflected at the interface 313 may also be totally internally reflected at the third face F3. Alternatively, a metallic or dielectric reflective coating may be formed on the third face F3.

The prism 302 may be made from a number of different materials of high refractive index. By way of example, and not by way of limitation, the prism 302 may be made may be cut from a sapphire wafer in a roughly triangular shape and the edges of the triangle may be polished to provide the faces F1, F2, and F3. To avoid two overlapping responses from each light source due to birefringence it may be desirable to orient the sapphire such that its optical axis (the so-called c-axis) is oriented perpendicular to the plane of the wafer from which the prism is formed.

The larger size of the prism 302 accommodates a larger lateral spacing D1 between the light sources 306A, 306B and a large lateral spacing D2 between light source 306B and the photodetector array 308. The larger size of the prism 302 and the large spacing D1 allows for a relatively small amount of overlap in the ranges of incidence angles for which light from the light sources 306A, 306B is totally internally reflected at the interface 313 but still allows each range of incidence angles to fill the photodetector array 308. Spreading the incidence angle ranges for each light source over the entire photodetector array allows for better resolution of refractive index since the incidence angles for total internal reflection at the interface 313 and the corresponding refractive indices are spread out over a greater number of pixels. The particular geometry shown in FIG. 3A allows for such improved resolution while allowing the light sources 306A, 306B and the photodetector array to be at roughly the same height relative to the plane of the common support (not shown). By way of example, the common support may be a printed circuit board, like the PCB 104 of FIG. 1A and FIG. 1B. For some applications it may be desirable to use a smaller light guiding structure while keeping a relatively large lateral spacing D1 between the light sources 306A, 306B and a large lateral spacing D2 between the light source 306B and the photodetector array. If the size of the photodetector array 308 remained the same as in FIG. 3A and the photodetector array and the light sources 306A, 306B were at the same height, this would lead to poorer resolution in refractive index since each range of incidence angles for total internal reflection at the interface 313 would be spread over a smaller number of pixels. However, this problem may be overcome by offsetting the relative height of the photodetector array 308 by a gap g relative to a height of light sources 306A, 306B. This puts the photodetector array 308 further from the first face F1 of the prism 302 as shown in the apparatus 300' depicted in FIG. 3B. In such a case, the desired range of refractive index may be measured without sacrificing resolution and without requiring that the light sources and photodetector array be at the same relative height.

It is noted that the optical sensor apparatus 300 depicted in FIG. 3A and the optical sensor apparatus 300' depicted in FIG. 3B may include other components described above, such as additional light sources, a memory, processor, and software. These components have been omitted from the drawing for the sake of clarity. Furthermore, although two light sources 306A, 306B are depicted in FIG. 3A and FIG. 3B, those skilled in the art will recognize that more than two light sources may be used. Furthermore, the light sources may include two or more common-wavelength light sources or two or more light sources that emit light at different vacuum wavelengths or some combination of these configurations of light sources.

Optical sensors of the type described herein have numerous advantages over competing concentration sensing technologies such as optical absorption. For example, because light is reflected rather than transmitted there are no problems with measuring the refractive index for opaque fluid samples. Furthermore, the sensor apparatus can be used with any material for the window. For example, in certain applications, such as pharmaceutical manufacturing, disposable bags made of transparent plastic may be used to provide the window.

In addition, calibration of a sensor apparatus of the type described herein is much easier than for an absorption spectroscopy sensor. If the sample under test is relatively simple it is not necessary to measure speciation. Calibration of the species of interest can be done by performing an auto-titration of the species of interest while measuring index of refraction with the sensor as a function of species concentration as determined by the auto-titration. By taking a derivative of irradiance versus pixel position for the calibration sample it is possible to determine refractive index of the calibration sample to within a small fraction of a pixel position. A run index of refraction measurements versus pixel position can be done for a series of samples of known concentration and the resulting calibration can be stored in memory 110. An offset in the calibration may be shifted by performing a run of measurements of irradiance versus pixel position for a reference sample, such as de-ionized water and re-zeroing the calibration.

A sensor apparatus of the type described herein can therefore compete with absorption spectrometry in the near IR or UV-visible wavelength ranges. The reflection geometry in the embodiments described herein also provides substantial advantages over sensors that use transmission geometry. For example, diffraction and adsorption effects can be eliminated, and the refractive indexes of opaque fluids can be measured.

While the above is a complete description of the preferred embodiments of the present invention, it is possible to use various alternatives, modifications, and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A" or "An" refers to a quantity of one or more of the item following the article, except where expressly stated otherwise. The appended claims are not to be interpreted as including means-plus-function limitations, unless such a limitation is explicitly recited in a given claim using the phrase "means for". Any element in a claim that does not explicitly state "means for" performing a specified function, is not to be interpreted as a "means" or "step" clause as specified in 35 USC §112, ¶6.

What is claimed is:

1. An optical sensor apparatus, comprising:
   an optically transmissive light guiding structure having planar first, second, and third faces;
   two or more light sources located outside the light guiding structure adjacent the first face;
   a photodetector array located outside the light guiding structure adjacent the first face, wherein the light guiding structure, light sources, and photodetector array are configured such that light from the two or more light sources that is totally internally reflected at an optical interface between the light guiding structure and a sample outside the light guiding structure proximate the second face is reflected at the third face and incident on a portion of the photodetector array that depends on a refractive index of the sample,
   wherein the two or more light sources are positioned with respect to the light guiding structure and photodetector array such that light from each of the two or more light sources that is totally internally reflected at the interface and reflected at the third face corresponds to a different range of refractive index of the sample and maps to a corresponding portion of the photodetector array.

2. The apparatus of claim 1, wherein the two or more light sources are separated from the light guiding structure by a free-space gap.

3. The apparatus of claim 1, wherein the photodetector array is separated from the light guiding structure by a free-space gap.

4. The apparatus of claim 1, wherein the two or more light sources include two or more common wavelength light sources configured to emit light of a common vacuum wavelength, wherein the two or more common wavelength light sources are positioned with respect to the light guiding structure and photodetector array such that light from each of the two or more common wavelength light sources that is totally internally reflected at the interface and reflected at the third face corresponds to a different range of refractive index of the sample and maps to a corresponding portion of the photodetector array.

5. The apparatus of claim 1, wherein the two or more light sources include two or more light sources configured to emit light of different corresponding vacuum wavelengths.

6. The apparatus of claim 5, further comprising a processor coupled to the photodetector array, wherein the processor is configured to determine an optical dispersion of the sample from measurements obtained by the photodetector array with light from the two or more light sources configured to emit light of different corresponding vacuum wavelengths that is totally internally reflected at the interface.

7. The apparatus of claim 1, wherein the two or more light sources, light guiding structure and photodetector array are configured such that light from the one or more light sources that is totally internally reflected at the interface passes through the first face a first time between leaving the one or more light sources and total internal reflection at the interface and passes through the first face a second time between the total internal reflection at the interface and arriving at the photodetector array.

8. The apparatus of claim 1, further comprising an optical window attached to the second face of the light guiding structure, wherein the optical window is characterized by a refractive index that is greater than a refractive index of the light guiding structure.

9. The apparatus of claim 8, wherein the light guiding structure is made of a material that is CTE-matched to the material of the window.

10. The apparatus of claim 8 wherein the light guiding structure is made of borosilicate glass and the window is made of sapphire.

11. The apparatus of claim 1, wherein the light guiding structure is configured such that light from the two or more light sources that is totally internally reflected at the optical interface is totally internally reflected at the third face.

12. The apparatus of claim 10, wherein the two or more light sources and the photodetector array are at substantially the same height relative to a supporting structure.

13. The apparatus of claim 10, wherein the two or more light sources are at substantially the same height relative to a supporting structure and a height of the photodetector array is offset with respect to the height of the two or more light sources.

14. The apparatus of claim 10, wherein the light guiding structure is made from a sapphire wafer.

15. The apparatus of claim 13, wherein an optical axis of the sapphire window is oriented perpendicular to a plane of the sapphire window.

* * * * *